United States Patent [19]
Wu et al.

[11] Patent Number: 6,133,494
[45] Date of Patent: Oct. 17, 2000

[54] CATALYST COMPOSITION COMPRISING ACID-BASE LEACHED ZEOLITES

[75] Inventors: An-hsiang Wu, Bartlesville; Charles A. Drake, Nowata, both of Okla.

[73] Assignee: Phillips Petroleum Company, Bartlesville, Okla.

[21] Appl. No.: 09/316,710

[22] Filed: May 21, 1999

Related U.S. Application Data

[62] Division of application No. 08/672,460, Jun. 26, 1996, Pat. No. 5,945,364.

[51] Int. Cl.[7] .............................. C07C 4/12; C10G 35/095
[52] U.S. Cl. ......................... 585/489; 585/470; 585/476; 585/486; 585/488; 585/489; 208/135
[58] Field of Search ..................................... 585/486, 488, 585/489, 470, 476; 208/135

[56] References Cited

U.S. PATENT DOCUMENTS

| | | | |
|---|---|---|---|
| 4,188,282 | 2/1980 | Tabak et al. | 208/134 |
| 4,224,141 | 9/1980 | Morrison et al. | 208/134 |
| 4,351,979 | 9/1982 | Chester et al. | 585/481 |
| 4,385,195 | 5/1983 | Butter et al. | 585/481 |
| 4,568,655 | 2/1986 | Oleck et al. | 502/66 |
| 5,001,296 | 3/1991 | Howley et al. | 585/489 |
| 5,030,787 | 7/1991 | Absil et al. | 585/475 |
| 5,160,500 | 11/1992 | Chu et al. | 585/486 |
| 5,800,696 | 9/1998 | Drake et al. | 208/135 |
| 5,804,059 | 9/1998 | Wu et al. | 208/135 |
| 5,827,422 | 10/1998 | Drake et al. | 208/135 |
| 5,866,744 | 2/1999 | Wu et al. | 585/486 |
| 5,905,051 | 5/1999 | Wu et al. | 502/60 |
| 5,922,630 | 7/1999 | Wu et al. | 502/64 |

*Primary Examiner*—Bekir L Yildirim
*Attorney, Agent, or Firm*—Reece A. Scott

[57] ABSTRACT

A catalyst composition and a process for hydrodealkylating $C_9+$ aromatic compounds such as, for example, trimethylbenzenes, to $C_6$ to $C_8$ aromatic hydrocarbons such as toluene and xylenes are disclosed. The composition comprises an alumina and a silica wherein the weight ratio of aluminum to silicon is in the range of from about 0.005:1 to about 0.25:1. The process comprises contacting, in the presence of the catalyst composition, a fluid which comprises a $C_9+$ aromatic compound with a hydrogen-containing fluid under a condition sufficient to effect the conversion of a $C_9+$ aromatic compound to a $C_6$ to $C_8$ aromatic hydrocarbon; and the $C_9+$ aromatic compound contains at least 9 carbon atoms. Also disclosed is a process for producing the catalyst composition which comprises: (1) contacting a zeolite with an effective amount of a base under a condition sufficient to effect a reduction in silicon content of said zeolite to produce a base-leached zeolite; and (2) contacting said base-leached zeolite with an effective amount of an acid under a condition sufficient to effect a reduction in aluminum content of said base-leached zeolite.

25 Claims, No Drawings

CATALYST COMPOSITION COMPRISING ACID-BASE LEACHED ZEOLITES

This application is a division of application Ser. No. 08/672,460 filed on Jun. 26, 1996 now U.S. Pat. No. 5,945,364.

FIELD OF THE INVENTION

This invention relates to a catalyst composition useful for converting $C_9+$ aromatic compounds to $C_6$ to $C_8$ aromatic hydrocarbons and to a process for using the composition.

BACKGROUND OF THE INVENTION

It is well known to those skilled in the art that aromatic hydrocarbons are a class of very important industrial chemicals which find a variety of uses in petrochemical industry. Recent efforts to convert gasoline to more valuable petrochemical products have therefore focused on the conversion of gasoline to aromatic hydrocarbons by catalytic cracking in the presence of zeolite catalysts. The aromatic hydrocarbons produced by the conversion process include benzene, toluene and xylenes (hereinafter collectively referred to as BTX) or $C_6$ to $C_8$ hydrocarbons, which can be useful feedstocks for producing various organic compounds and polymers. However, heavier, less useful aromatic compounds are also produced during the conversion process. Therefore, a catalyst and a process for converting these heavier and less useful aromatic compounds (mainly trimethyl- and tetramethylbenzenes) to the more valuable BTX hydrocarbons would be a significant contribution to the art and to the economics.

SUMMARY OF THE INVENTION

An object of this invention is to provide a catalyst composition which can be used to convert $C_9+$ aromatic compounds to $C_6$ to $C_8$ aromatic hydrocarbons. Also an object of this invention is to provide a process for producing the catalyst composition. Another object of this invention is to provide a process which can employ the catalyst composition to convert $C_9+$ aromatic compounds to $C_6$ to $C_8$ aromatic hydrocarbons. An advantage of the catalyst composition is that it exhibits high hydrodealkylation activity, satisfactory selectivity to xylenes, and good stability. Other objects and advantages will becomes more apparent as this invention is more fully disclosed hereinbelow.

According to a first embodiment of the present invention, a composition which can be used as a catalyst for converting a $C_9+$ aromatic compound to a $C_6$ to $C_8$ aromatic hydrocarbon is provided. The composition is an aluminosilicate which comprises, a silica, an alumina, and optionally platinum wherein the weight ratio of elemental aluminum to elemental silicon is in the range of from about 0.005:1 to about 0.25:1 and the weight ratio of the optimal platinum to silicon is in the range of from about 0.0005:1 to about 0.01:1.

According to a second embodiment of the present invention, a process which can be used for producing a catalyst composition is provided. The process comprises the steps: (1) contacting a zeolite which comprises or consists essentially of a silica and an alumina with a base in an amount and under a condition effective to reduce the silica content of the zeolite to produce a silica-reduced zeolite; (2) contacting said silica-reduced zeolite with an acid in an amount and under a condition effective to reduce the alumina content of the silica-reduced zeolite to produce an alumina-reduced zeolite; and optionally (3) contacting the alumina-reduced zeolite with a platinum precursor.

According to a third embodiment of the present invention, a process which can be used for converting a $C_9+$ aromatic compound to a $C_6$ to $C_8$ aromatics compound is provided which comprises, consists essentially of, or consists of, contacting a fluid which comprises a $C_9+$ aromatic compound with a hydrogen-containing fluid in the presence of a catalyst composition which is the same as disclosed above in the first embodiment of the invention under a condition effective to convert a $C_9+$ aromatic compound to an aromatic hydrocarbon containing 6 to 8 carbon atoms per molecule.

DETAILED DESCRIPTION OF THE INVENTION

The catalyst composition of the first embodiment of the present invention can comprise a silica and an alumina. The catalyst composition can also comprise, consist essentially of, or consist of a silica, alumina, and platinum.

According to the present invention the weight ratio of element aluminum to element silicon can be in the range of from about 0.002:1 to about 0.25:1, preferably about 0.004:1 to about 0.2:1, more preferably about 0.005:1 to about 0.15:1, and most preferably 0.01:1 to 0.1:1. The weight ratio of element platinum to element silicon can be in the range of from about 0.0001:1 to about 0.02:1, preferably about 0.0005:1 to about 0.02:1, more preferably about 0.001:1 to about 0.02:1, and most preferably 0.002:1 to 0.01:1.

Alternatively, the weight of element aluminum in the invention composition can be in the range of from about 0.1 to about 10, preferably about 0.2 to about 8, and most preferably 0.5 to 5 grams per 100 grams of the composition. The weight of element silicon can be in the range of from about 25 to about 45, preferably about 30 to about 45, and most preferably 35 to 40 grams per 100 grams of the composition. The weight of platinum can be in the range of from about 0.01 to about 2, preferably about 0.05 to about 1.5, and most preferably 0.1 to 1.2 grams per 100 grams of the composition. The composition can also be characterized by having the following physical characteristics: a surface area as determined by the BET method using nitrogen in the range of from about 300 to about 600, preferably 350 to 500 $m^2/g$; a pore volume in the range of from about 0.4 to about 0.8, preferably about 0.5 to about 0.75, and most preferably 0.6 to 0.75 ml/g; an average pore radius in the range of from about 70 to about 300, preferably about 100 to about 250, and most preferably 125 to 200 Å; and a porosity of more than about 50%. Detailed physical property analyses are disclosed hereinbelow in the Examples section.

The composition of the present invention can be prepared by combining any alumina and any silica in the element weight ratios disclosed above under any conditions sufficient to effect the formation of an aluminosilicate.

If the presence of platinum in the composition is desired, a platinum-containing compound can be combined with any alumina and any silica in the element weight ratios disclosed above under a condition sufficient to effect the formation of a platinum-containing aluminosilicate. Alternatively, an aluminosilicate prepared above can be contacted with a platinum-containing compound under a condition sufficient to effect the formation of a platinum-containing aluminosilicate.

Generally, any platinum-containing compound that can promote the combining of platinum element with an aluminosilicate can be employed herein. Examples of suitable platinum-containing compounds include, but are not limited to, chloroplatinic acid ($H_2PtCl_6 \cdot xH_2O$), platinum (IV) chloride (platinic chloride), platinum (II) bromide, platinum (II) iodine, tetramine platinum (II) chloride ($Pt(NH_3)_4Cl_2 \cdot H_2O$ or $Pt(NH_3)_4Cl_2$), tetramine platinum (II) nitrate ($Pt(NH_3)_4(NO_3)_2$), tetramine platinum (II) hydroxide ($Pt(NH_3)_4(OH)_2$), tetrachlorodiamne platinum (IV), and combinations of any two or more thereof. The presently preferred platinum-containing compound is chloroplatinic acid for it is readily available.

Generally, the combining of a platinum-containing compound with an alumina and a silica or with an aluminosilicate can be carried out by any method known to one skilled in the art. For example, an aluminosilica or a physical mixture of an alumina and a silica can be combined with a solution containing a platinum-containing compound, preferably an aqueous solution, under a condition sufficient to effect the soaking or impregnating of platinum by the mixture of alumina and silica or by the aluminosilicate followed by removing the liquid, generally by heating at a temperature in the range of from about 400° C. to about 1000° C., preferably 450° C. to 800° C. for a sufficient time to remove all liquid, generally depending on the amount of liquid to be removed and the heating temperature. Upon completion of impregnating the platinum, the platinum-impregnated aluminosilicate can be, if desired, treated with a reducing agent to reduce the oxidation state of platinum to 0. The presently preferred reducing agent is a hydrogen-containing fluid which comprises molecular hydrogen ($H_2$) in the range of from 1 to about 100, preferably about 5 to about 100, and most preferably 10 to 100 volume %. The reduction can be carried out at a temperature, in the range of from about 250° C. to about 800° C. for about 0.1 to about 10 hours preferably about 300° C. to about 700° C. for about 0.5 to about 7 hours, and most preferably 350° C. to 550° C. for 1 to 5 hours. If the calcined platinum-impregnated composition is not first treated with a reducing agent, the composition of the present invention can be treated with a reducing agent as described above prior to use of the composition of the invention.

However, it is presently preferred that the composition of the present invention be produced by the process disclosed in the second embodiment of the invention. In the first step of the second embodiment of the invention, a zeolite is contacted with a base under a condition sufficient to effect the formation of an silica-reduced zeolite.

Any commercially available zeolites can be employed as a starting material of the process of the second embodiment of the invention. Examples of suitable zeolites include, but are not limited to, those disclosed in Kirk-Othmer Encyclopedia of Chemical Technology, third edition, volume 15 (John Wiley & Sons, New York, 1991) and in W. M. Meier and D. H. Olson, "Atlas of Zeolite Structure Types," 138–139, Butterworth-Heineman, Boston, Mass., (3rd ed. 1992). ZSM-5 and similar zeolites that have been identified as having a framework topology identified as MFI are particularly preferred because of their shape selectivity.

According to the present invention, any base can be employed so long as the base can reduce the silica content of a zeolite. Examples of suitable base include, but are not limited to, tetramethylammonium hydroxide, tetraethylammonium hydroxide, tetrapropylammonium hydroxide, tetramethylammonium bisulfide, tetraethylammonium bisulfide, lithium hydroxide, sodium hydroxide, sodium hydrosulfide, sodium bisulfide, potassium hydroxide, calcium hydroxide, magnesium hydroxide, sodium bicarbonate, sodium carbonate, sodium oxide, sodium sulfide, magnesium oxide, calcium oxide, calcium carbonate, sodium phenoxide, barium phenoxide, calcium phenoxide, $R^1OM$, $R^1SM$, and combinations of any two or more thereof; where $R^1$ is a $C_1$–$C_{18}$ alkyl radical, or combinations of any two or more thereof and M is an alkali metal, an alkaline earth metal, or combinations of any two or more thereof. Among the bases, sodium hydroxide and sodium carbonate are preferred because they are readily available and inexpensive.

According to the present invention, any methods known to one skilled in the art to treat a solid catalyst with a base can be used to treat the raw zeolite material. Generally, a zeolite can be suspended in a solution comprising a base substantially dissolved or suspended therein. The concentration of the zeolite in the solution to prepare a suspension can be in the range of from about 0.01 to about 200, preferably about 0.1 to about 150, more preferably about 1 to about 100, and most preferably 5 to 75 grams per liter. The amount of base required is the amount that can maintain the solution in alkaline pH during the treatment. Preferably, the initial pH of the solution containing a zeolite is adjusted to above about 8, preferably above about 10, and most preferably above 12. Upon the pH adjustment of the solution, the solution can be subjected to a treatment at a temperature in the range of from about 30° C. to about 200° C., preferably about 50° C. to about 150° C., and most preferably 70° C. to 120° C. for about 10 minutes to about 30 hours, preferably about 30 minutes to about 25 hours, and most preferably 1 to 20 hours. The treatment can be carried out under a pressure in the range of from about 1 to about 10 atmospheres (atm), preferably about 1 atm. Thereafter, the treated zeolite can be washed with a running water for 1 to about 60 minutes followed by drying to produce a silica-reduced or base-leached zeolite. Any drying method known to one skilled in the art such as, for example, air drying, heat drying, spray drying, fluidized bed drying, or combinations of two or more thereof can be used.

The dried, silica-reduced zeolite can also be further washed, if desired, with a mild acid solution such as, for example, ammonium nitrate which is capable of bringing the pH of the wash to an acidic range. The volume of the acid generally can be the same volume as the base required to bring the pH to the range disclosed above. The mild acid treatment can be carried out under substantially the same conditions disclosed in the base treatment. Thereafter, the resulting solid can be washed and dried as disclosed above.

According to the second embodiment of the present invention, the base-leached or silica-reduced zeolite is subject to an acid treatment. Generally, the acid can be organic acids, inorganic acids, or combinations of any two or more thereof. The acid can also be a diluted aqueous acid solution. Examples of suitable acids include, but are not limited to sulfuric acid, hydrochloric acid, nitric acid, phosphoric acid, ammonium sulfate, ammonium chloride, ammonium nitrate, formic acid, acetic acid, trifluoroacetic acid, citric acid, trichloroacetic acid, p-toluenesulfonic acid, methanesulfonic acid, partially neutralized acids, wherein one or more protons have been replaced with, for example, a metal (preferably an alkali metal), and combinations of any two or more thereof. Examples of partially neutralized acids include, but are not limited to, sodium bisulfate, sodium dihydrogen phosphate, potassium hydrogen tartarate, and combinations thereof. The presently preferred acids are hydrochloric acid and nitric acid for they are readily available.

Any methods known to one skilled in the art for treating a solid catalyst with an acid can be used in the acid treatment of the present invention. Generally, the silica-reduced or base-leached zeolite can be suspended in an acid solution. The concentration of the base-leached zeolite in the acid solution can be in the range of from about 0.01 to about 200, preferably about 0.1 to about 150, more preferably about 1 to about 100, and most preferably 5 to 75 grams per liter. The amount of acid required is the amount that can maintain the solution in acidic pH during the treatment. Preferably the initial pH of the acid solution containing a base-reduced zeolite is adjusted to lower than about 3, preferably lower than about 2, more preferably lower than about 1, and most preferably lower than 0.5. Upon the pH adjustment of the solution, the solution can be subjected to a treatment at a temperature in the range of from about 30° C. to about 200° C., preferably about 50° C. to about 150° C., and most preferably 70° C. to 120° C. for about 10 minutes to about 30 hours, preferably about 30 minutes to about 25 hours, and most preferably 1 to 20 hours. The treatment can be carried out under a pressure in the range of from about 1 to about 10 atmospheres (atm), preferably about 1 atm. Thereafter, the treated zeolite can be washed with a running water for 1 to about 60 minutes followed by drying to produce an alumina-reduced or base-acid-leached zeolite. Any drying method known to one skilled in the art such as, for example, air drying, heat drying, spray drying, fluidized bed drying, or combinations of two or more thereof can be used.

The dried, alumina-reduced zeolite can also be further washed, if desired, with mild acid solution such as, for example, ammonium nitrate which is capable of bringing the pH of the wash to acidic range. The volume of the acid generally can be the same volume as the base required to bring the pH to the range disclosed above. The mild acid treatment can be carried out under substantially the same conditions disclosed in the base treatment. Thereafter, the resulting solid can be washed and dried as disclosed above.

The base-acid-leached zeolite can then be treated with a platinum-containing compound to produce a platinum-impregnated composition of the invention. The treatment with a platinum-containing compound is the same as that disclosed above except the starting material herein is a base-acid-leached zeolite. The platinum-impregnated composition can be treated with a reducing agent, if desired, as disclosed above.

According to the third embodiment of the present invention, a process useful for converting a $C_9+$ aromatic compound to a $C_6$ to $C_8$ aromatic hydrocarbon comprises, consists essentially of, or consists of contacting a fluid stream comprising a $C_9+$ aromatic compound, in the presence of a catalyst composition, with a hydrogen-containing fluid under a condition sufficient to effect the conversion of a $C_9+$ aromatic compound to a $C_6$ to $C_8$ aromatic hydrocarbon. The catalyst composition is the same as that disclosed in the first embodiment of the invention. The term "fluid" is used herein to denote gas, liquid, vapor, or combination thereof. The term "$C_9+$ aromatic compound" is referred to, unless otherwise indicated, as a substituted aromatic compound containing at least 9 carbon atoms per molecule. Preferably the substituted aromatic compound has the formula of $R_nAr$ wherein each R is a hydrocarbyl radical having 1 to about 15 carbon atoms and is independently selected from the group consisting of alkyl radicals, aryl radicals, alkaryl radicals, aralkyl radicals, alkenyl radicals, and combinations of any two or more thereof, n is a whole number from 1 to 5, and Ar is an aryl group, preferably a phenyl group. More preferably R is an alkyl radical having 1 to about 10 carbon atoms and the aromatic compound has 9 to about 16 carbon atoms per molecule. Most preferably the aromatic compound contains 9 to 12 carbon atoms per molecule.

Any fluid which contains a $C_9+$ aromatic compound as disclosed above can be used as the feed for the process of this invention. The origin of this fluid feed is not critical. However, a preferred fluid feed is a $C_9+$ aromatic compound derived from the heavies fraction of a product from a paraffin, in particular gasoline, aromatization reaction. Generally, this heavies fraction contains primarily trimethylbenzenes such as 1,2,3-trimethylbenzene, 1,2,4-trimethylbenzene, and 1,3,5-trimethylbenzene and tetramethylbenzenes such as 1,2,3,4-tetramethylbenzene, 1,2,3,5-tetramethylbenzene and 1,2,4,5-tetramethylbenzene. Additionally, n-propylbenzene, 3-ethyltoluene, 4-ethyltoluene, 3-n-propyltoluene, 4-n-propyltoluene, and 1,3-diethylbenzene can also be present in the fluid. Benzene, toluene, ethylbenzene and xylenes are generally substantially absent from the fluid, i.e., the amount of each of these aromatic hydrocarbons is less than about 0.1 weight %. Thus, there is no significant alkylation of these lower aromatic hydrocarbons by the $C_9+$ aromatic compound, i.e., no significant transalkylation occurs as a side-reaction in the process of this invention.

Any hydrogen-containing fluid which comprises, consists essentially of, or consists of, molecular hydrogen ($H_2$) can be used in the process of this invention. This hydrogen-containing fluid can therefore contain $H_2$ in the range of from about 1 to about 100, preferably about 5 to about 100, and most preferably 10 to 100 volume %. If the $H_2$ content in the fluid is less than 100%, the remainder of the fluid may be any inert gas such as, for example, $N_2$, He, Ne, Ar, or combinations of any two or more thereof, or any other fluid which does not significantly affect the process or the catalyst composition used therein.

The contacting of a fluid containing a $C_9+$ aromatic compound and a hydrogen-containing fluid in the presence of the catalyst composition can be carried out in any technically suitable manner, in batch, semicontinuous, or continuous process under a condition effective to convert a $C_9+$ aromatic compound to a $C_6$ to $C_8$ aromatic hydrocarbon. Generally, a fluid containing a $C_9+$ aromatic compound, preferably being in the vaporized state, and a hydrogen-containing fluid are introduced into a fixed catalyst bed, or a moving catalyst bed, or a fluidized catalyst bed, or combinations of any two or more thereof by any means known to one skilled in the art such as, for example, pressure, meter pump, and other similar means. The condition can include an hourly space velocity (HSV) of the $C_9+$ aromatic compound fluid stream in the range of about 0.01 to about 100, preferably about 0.05 to about 50, and most preferably 0.1 to 30 g feed/g catalyst/hour. The hydrogen-containing fluid hourly space velocity generally is in the range of about 1 to about 10,000, preferably about 5 to about 7,000, and most preferably 10 to 5,000 $ft^3$ $H_2/ft^3$ catalyst/hour. The preferred molar ratio of $H_2$ to the $C_9+$ aromatic compound can be in the range of from about 0.01:1 to about 20:1, preferably about 0.1:1 to about 10:1, and most preferably 0.5:1 to 5:1. Generally, the pressure can be in the range of from about 30 to about 1000 psig, preferably about 50 to about 750 psig, and most preferably 200 to 600 psig, and the temperature is about 250 to about 1,000° C., preferably about 450 to about 750° C.

The process effluent generally contains a heavies fraction of unconverted $C_9+$ aromatics and other heavy ($C_9+$) aromatic compounds which may have been formed by side-reactions (such as isomerization); a lights fraction of alkanes, mainly methane, ethane, propane, n-butane, isobutane, and minor amounts (about 0.1 to about 5 weight %) of $C_5$ alkanes (isopentane and n-pentane); and a BTX aromatic hydrocarbons fraction (benzene, toluene, ortho-xylene, meta-xylene and para-xylene). Generally, the effluent can be separated into these principal fractions by fractionation distillation which is well known to one skilled in the art. The heavies fraction can be recycled to a hydrodealkylation reactor described above, the lights fraction can be used as fuel gas or as a feed for other reactions such as, for example, in a thermal cracking process to produce ethylene and propylene, and the BTX fraction can be further separated into individual $C_6$ to $C_8$ aromatic hydrocarbon fractions. Alternatively, the BTX fraction can undergo one or more reactions either before or after separation to individual $C_6$ to $C_8$ hydrocarbons so as to increase the content of the most desired BTX aromatic hydrocarbon. Suitable examples of such subsequent $C_6$ to $C_8$ aromatic hydrocarbon conversions are disproportionation of toluene (to form benzene and xylenes), transalkylation of benzene and xylenes (to form toluene), and isomerization of meta-xylene and/or ortho-xylene to para-xylene.

After the catalyst composition has been deactivated by, for example, coke deposition or feed poisons, to an extent that the feed conversion and/or the selectivity to the most valuable $C_6$ to $C_8$ aromatic product (generally xylenes) have become unsatisfactory, the catalyst composition can be reactivated by any means known to one skilled in the art such as, for example, calcining in air to burn off deposited coke and other carbonaceous materials, such as oligomers or polymers, preferably at a temperature of about 400 to about 650° C., followed by a treatment with a reducing agent such as, for example, with hydrogen gas at a temperature of about 400 to about 600° C. The optimal time periods of the calcining and treatment with a reducing agent depend generally on the types and amounts of deactivating deposits on the catalyst composition and on the calcination and reduction temperatures. These optimal time periods can easily be determined by those possessing ordinary skills in the art and are omitted herein for the interest of brevity.

The following examples are presented to further illustrate this invention and are not to be construed as unduly limiting the scope of the present invention.

EXAMPLE I

This example illustrates the preparation of catalyst composition of the invention.

A zeolite HZSM-5 purchased from UCI (United Catalysts, Inc., Louiville, Ky.) having a designate of T-4480 (obtained as a 1/16 inch extrudate) was used in the preparation of the catalyst composition of the invention. Thirty grams of T-4480 were added to 200 g of a basic solution in a beaker, wherein the basic solution was prepared by mixing 172 g of $Na_2CO_3.10H_2O$, 4 g of NaOH, and 500 g of water, to prepare a suspension having a pH of 13. The suspension was then heated at 90° C. for 6 hours to prepare a base-treated zeolite. Thereafter, the spent basic solution was discarded by decantation. The base-treated zeolite was then washed with a running tap water for about 30 minutes. The washed, base-treated zeolite was then air-dried at room temperature (about 25 ° C.). The air-dried, base-treated zeolite was then treated with 200 ml of a 1.0 M $NH_4NO_3$ solution for 16 hours at 90° C. to prepare a nitrated-treated, base-treated zeolite which upon discarding the spent nitrate solution, was then washed with a running tap water for about 30 minutes followed by air drying. The air-dried material was then subject to calcining at 525° C. for 3 hours to prepare a silica-reduced or base-leached zeolite. A total of 14.08 g of the silica-reduced or base-leached zeolite was produced.

The silica-reduced zeolite was then combined with 180 g of 6N HCl and the resulting suspension was heated at 90° C. for 2 hours to prepare a base-acid-treated zeolite which was subject to washing and drying as described above and to calcining at 525° C. for 6 hours. The resulting dried product (10.56 g) was an alumina-reduced or base-acid-leached zeolite or the composition of the invention.

In separate runs, 7.04 grams of silica-reduced zeolite obtained as described above was impregnated with 4.18 g of an aqueous solution containing 0.5 weight % chloroplatinic acid ($H_2PtCl_6.xH_2O$; CPA) following by calcining with a hot air in a furnace at 525° C. for 6 hours to produce a platinum-promoted, silica-reduced zeolite (total weight= 7.16 g). A platinum-promoted, alumina-reduced zeolite (5.30 g) was similarly obtained by impregnating 5.28 g of the alumina-reduced or base-acid-leached zeolite with 4.57 g of CPA.

In comparative runs, 32.0 g of T-4480 was combined with 100 g of 6N HCl in a beaker to form a suspension. The suspension was heated at 90° C. for 2 hours. Upon decantation of spent HCl solution, the solid was washed, dried, and calcined as described above to produce 22.64 g of acid-leached zeolite.

Also in comparative runs, 30.0 g of T-4480 was combined with 230 ml of 3N HCl to form a suspension. The suspension was heated at 90° C. for 6 hours. Upon removal of spent HCl solution, the resulting solid was washed, dried, and calcined as described above to prepare a calcined zeolite (21.2 g) that had been treated with HCl. The calcined zeolite was then combined with 180 ml of 0.5N NaOH solution to form another suspension. However, upon the combining, a white, cloudy, milky solution formed indicating that the calcined zeolite dissolved in NaOH solution.

The above-produced zeolites including the original ZSM-5 (T-4480) zeolite and the invention catalyst composition were further analyzed for their surface area, pore volume, and pore radius (Table I) as well as the weight % of individual component (Table II).

The unit cell dimension (also referred to as unit cell size; measured in angstroms) was determined by X-ray diffraction, essentially in accordance with ASTM D 3942-80.

The ratio of Si atoms to Al atoms in the crystalline zeolite framework portion was determined by Si solid state NMR spectrometry, substantially in accordance with the procedure described by J. Klinowski et al in Nature, April 1982, Volume 296, pages 533–536. The Si:Al atomic ratio (or Si/Al) in the crystalline framework portion for the invention composition was found between 22.0 and 25.7.

Because zeolites generally also contain a substantially amorphous silica-alumina portion besides the crystalline zeolite portion, the total Si content and the total Al content were determined by X-ray fluorescence spectrometry employing a Siemens MRS 400 multi-channel spectrometer.

The surface area was determined in accordance with a modified $BET/N_2$ method (ASTM method D 3037), wherein the relative partial pressure of the gas phase, $p/p_o$ was in the range of about 0.01–0.06 ($p=N_2$ partial pressure in the gas phase, at the test conditions; $p_o$=vapor pressure of $N_2$ at its boiling point under the test conditions).

Pore volume was determined by mercury intrusion porosimetry carried out at room temperature and a mercury pressure ranging from an initial pressure of 0 psig to a final pressure of 60,000 psig using an Autopore 9200 instrument of Micromeritics, Norcross, Ga. The average pore diameter was calculated by first dividing the pore volume by surface area to obtain a number Q and then multiplying Q by 4.

These analytical methods are well known to those skilled in the art and have been disclosed in U.S. Pat. Nos. 4,663,025 and 4,975,399, disclosures of which are incorporated herein by reference.

TABLE I

Sorption Data

|  | T-4480 | Acid-leached T-4480 | Base-leached T-4480 | Invention Composition |
|---|---|---|---|---|
| Surface Area (m²/g) | | | | |
| micro- | 212.10 | 285.30 | 227.80 | 308.50 |
| meso- | 174.20 | 148.60 | 170.70 | 157.00 |
| BET | 386.30 | 433.90 | 398.50 | 465.40 |
| Pore Volume (ml/g) | | | | |
| micro | 0.0898 | 0.1203 | 0.0939 | 0.1268 |
| meso- | 0.4492 | 0.6829 | 0.4035 | 0.6269 |
| Total | 0.5351 | 0.5806 | 0.5294 | 0.6856 |
| Avg Pore Radius (Å) | | | | |
| micro- | 28 | 27 | 27 | 29 |
| meso | 63 | 157 | 62 | 166 |
| Porosity (%) | 48.48 | 55.33 | 43.99 | 50.31 |

Microproe size <20Å
Mesoproe size 20–500Å
Macroproe size >500Å

The results shown in Table I demonstrate that the composition of the present invention had significantly higher surface area, pore volume, and pore radius than the original zeolite T-4480, or acid-leached T-4480, or base-leached T-4480.

TABLE II

Element Weight %[a]

|  | T-4480 | Acid-leached T-4480 | Base-leached T-4480 | Invention Composition |
|---|---|---|---|---|
| Aluminum | 12.80 | 3.10 | 12.70 | 2.50 |
| Silicon | 32.10 | 40.50 | 30.90 | 38.70 |
| Platinum | 0.10 | 0.16 | 0.11 | 0.16 |
| Sodium | 0.11 | 0.12 | 0.32 | 0.15 |
| Magnesium | 0.31 | 0.18 | 0.30 | 0.15 |
| Calcium | 0 | 0 | 0.08 | 0 |

[a]The atomic weight % is expressed as 100% times the element weight divided by the total weight of the respective zeolites.

Table II shows that acid-leached zeolite had considerably reduced aluminum (and thus alumina) content and that silicon (and therefore silica) content was reduced by base-treatment. Because acid treatment significantly reduced the aluminum content, the invention composition showed a relatively-increased silicon content as compared to T-4480.

EXAMPLE II

This example illustrates the use of the catalyst composition described in Example I as catalysts in the hydrodealkylation of a $C_9+$ aromatic compound to BTX.

A stainless-steel reactor tube (inner diameter 0.75 inch; length: 20 inches) was filled with a 5 cc bottom layer of Alundum® alumina (inert, low surface area alumina) 10 cc of one of the catalysts, and a 5 cc top layer of Alundum® alumina. The catalyst was pretreated with flowing hydrogen gas (flow rate: 260 cc $H_2$ per minute) at a temperature being raised from room temperature to a final temperature of 450° C. at a rate of 10° C. per minute. Then the liquid feed, which contained $C_9+$ aromatic compounds, was introduced at a rate of 40 cc/hour, together with hydrogen gas at a rate of 260 cc $H_2$/minute. The liquid hourly space velocity of the feed was about 4 cc feed/cc catalyst/hour (equivalent to a weight hourly space velocity of about 5.5–6 g feed/g catalyst/hour). The reaction temperature was 550° C. and the reaction pressure was 500 psig. The reactor effluent was cooled and separated into a gaseous phase and a liquid phase. Both phases were analyzed by gas chromatographs at intervals of about 1 hour.

The liquid feed in two hydrodealkylation runs was heavy $C_9+$ aromatic compounds obtained in a gasoline aromatization test. The composition of the feed is given in Table III which contained less than 2 ppm S. Not given in Table III are numerous components which were in very small quantities and, in some instances, whose chemical structures were unknown.

TABLE III

Composition of Feed

| Feed Component | Weight Percent |
|---|---|
| c-Hexene-2 | 1.104 |
| 1-Methyl-3-ethylbenzene | 2.254 |
| 1-Methyl-4-ethylbenzene | 1.057 |
| 1,3,5-Trimethylbenzene | 1.958 |
| 1-Methyl-2-ethylbenzene | 1.306 |
| 1,2,4-Trimethylbenzene | 9.977 |
| 1,2,3-Trimethylbenzene | 3.060 |
| 1-Methyl-3-i-propylbenzene | 0.286 |
| 2,3-dihydroindene | 2.845 |
| 1,3-Diethylbenzene | 1.173 |
| 1-Methyl-3-n-propylbenzene | 1.543 |
| 1,4-Diethylbenzeneylbenzene | 0.910 |
| 1-Methyl-4-n-propylbenzene | 0.328 |
| n-Butylbenzene-ethylbenzene | 2.836 |
| 1-Methyl-2-n-propylbenzene | 0.889 |
| 1,4,-Dimethyl-2-ethylbenzene | 1.991 |
| s-C5-benzene/1,3-dimethyl-4-ethylbenzene | 2.958 |
| 1,2-Dimethyl-4-ethylbenzene | 3.454 |
| 1,2-Dimethyl-3-ethylbenzene | 1.007 |
| 1,2,4,5-Tetramethylbenzene | 1.936 |
| 1,2,3,5-Tetramethylbenzene | 2.695 |
| 5-Methylindan | 3.004 |
| 1-Ethyl-2-n-propylbenzene | 1.592 |
| 2-Methylindan | 3.040 |
| 1,3-Di-i-propylbenzene | 1.084 |
| Naphthalene | 4.767 |
| 2-Methylnaphthalene | 3.382 |
| 1-Methylnaphthalene | 1.184 |

Table IV below illustrates the production of BTX from the Table III feed and individual catalyst compositions produced in Example I.

TABLE IV

BTX Production

| Time | T-4480 | Acid-leached T-4480 | Base-leached T-4480 | Invention Composition |
|---|---|---|---|---|
| 2 | 50.5 | 50.3 | 55.7 | 57.9 |
| 3 | 50.5 | 48.8 | 44.1 | 57.6 |
| 4 | 46.0 | 44.4 | 35.3 | 57.4 |
| 5 | 47.4 | 41.1 | 33.2 | 56.6 |
| 6 | 43.1 | 43.9 | 32.5 | 56.6 |
| 7 | 43.4 | 42.5 | 28.2 | 56.7 |
| 8 | not determined | 40.1 | not determined | 56.1 |

The results presented in Table IV demonstrate that, during the course of the hydrodealkylation process, the invention composition produced significantly more BTX than other zeolites shown in the table.

Reasonable variations, modifications and adaptations for various usages and conditions can be made within the scope of the disclosure and the appended claims, without departing from the scope of this invention.

That which is claimed:

1. A process comprising contacting, in the presence of a catalyst composition, a fluid which comprises at least a $C_9+$ aromatic compound with a hydrogen-containing fluid under a condition sufficient to effect the conversion of a $C_9+$ aromatic compound to a $C_6$ to $C_8$ aromatic hydrocarbon wherein said catalyst composition is prepared by a process comprising: (1) contacting a zeolite with a base to effect a reduction in silicon content of said zeolite to produce a base-leached zeolite; and (2) contacting said base-leached zeolite with an acid to effect a reduction in aluminum content of said base-leached zeolite to thereby provide a base-acid-leached zeolite; and further wherein said $C_9+$ aromatic compound contains at least 9 carbon atoms.

2. A process according to claim 1 wherein said $C_9+$ aromatic compound has the formula of $R_nAr$ wherein each R is a hydrocarbyl radical having 1 to about 15 carbon atoms and is independently selected from the group consisting of alkyl radicals, aryl radicals, alkaryl radicals, aralkyl radicals, alkenyl radicals, and combinations of any two or more thereof, n is a whole number from 1 to 5, and Ar is an aryl group.

3. A process according to claim 2 wherein R is an alkyl radical and said $C_9+$ aromatic compound contains 9 to 12 carbon atoms per molecule.

4. A process according to claim 3 wherein said $C_9+$ aromatic compound comprises an aromatic hydrocarbon selected from the group consisting of 1,2,3-trimethylbenzene, 1,2,4-trimethylbenzene, 1,3,5-trimethylbenzene, 1,2,3,4-tetramethylbenzene, 1,2,3,5-tetramethylbenzene, 1,2,4,5-tetramethylbenzene, n-propylbenzene, 3-ethyltoluene, 4-ethyltoluene, 3-n-propyltoluene, 4-n-propyltoluene, 1,3-diethylbenzene, and combinations of any two or more thereof.

5. A process according to claim 4 wherein said condition comprises a liquid hourly space velocity of said fluid in the range of about 0.1 to about 30 g feed/g catalyst/hour, a gas hourly space velocity of said hydrogen-containing fluid in the range of about 10 ft$^3$ gas/ft$^3$ catalyst/hour to about 5,000 ft$^3$ gas/ft$^3$ catalyst/hour, a molar ratio of hydrogen to said $C_9+$ aromatic compound in the range of about 0.5:1 to about 5:1, a pressure in the range of about 50 psig to about 750 psig, and a temperature in the range of about 250° C. to about 750° C.

6. A process according to claim 5 wherein said base-acid-leached zeolite is contacted with a platinum-containing compound; and further wherein said base is selected from the group consisting of tetramethylammonium hydroxide, tetraethylammonium hydroxide, tetrapropylammonium hydroxide, tetramethylammonium bisulfide, tetraethylammonium bisulfide, lithium hydroxide, sodium hydroxide, sodium hydrosulfide, sodium bisulfide, potassium hydroxide, calcium hydroxide, magnesium hydroxide, sodium bicarbonate, sodium carbonate, sodium oxide, sodium sulfide, magnesium oxide, calcium oxide, calcium carbonate, sodium phenoxide, barium phenoxide, calcium phenoxide, $R^1OM$, $R^1SM$ and combinations of any two or more thereof where $R^1$ is a $C_1$–$C_{18}$ alkyl radical and combinations of any two or more thereof and M is an alkali metal, an alkaline earth metal, and combinations of any two or more thereof.

7. A process according to claim 6 wherein said platinum-containing compound is selected from the group consisting of chloroplatinic acid, platinum (IV) chloride, platinum (II) bromide, platinum (II) iodine, tetramine platinum (II) chloride, tetramine platinum (II) nitrate, tetramine platinum (II) hydroxide, tetrachlorodiamne platinum (IV), and combinations of any two or more thereof; and further wherein said base is selected from the group consisting of sodium hydroxide, sodium carbonate, and combinations of any two or more thereof.

8. A process according to claim 7 wherein said acid is selected from the group consisting of sulfuric acid, hydrochloric acid, nitric acid, phosphoric acid, ammonium sulfate, ammonium chloride, ammonium nitrate, formic acid, acetic acid, trifluoroacetic acid, citric acid, trichloroacetic acid, p-toluenesulfonic acid, methanesulfonic acid, partially neutralized acids wherein one or more protons thereof have been replaced with a metal, and combinations of any two or more thereof.

9. A process according to claim 8 wherein said acid is selected from the group consisting of hydrochloric acid, nitric acid, and combinations of any two or more thereof; and further wherein said platinum-containing compound is chloroplatinic acid.

10. A process according to claim 9 wherein said step (1) and said step (2) of said process are carried out in an aqueous solution.

11. A process according to claim 10 wherein the pH of said aqueous solution in said step (1) is higher than about 8.

12. A process according to claim 11 wherein the pH of said aqueous solution in said step (1) is higher than 12.

13. A process according to claim 12 wherein the pH of said aqueous solution in said step (2) is lower than about 3.

14. A process according to claim 13 wherein the pH of said aqueous solution in said step (2) is lower than 0.5.

15. A process comprising contacting, in the presence of a catalyst composition, a fluid which comprises at least a $C_9+$ aromatic compound with a hydrogen-containing fluid under a condition sufficient to effect the conversion of a $C_9+$ aromatic compound to a $C_6$ to $C_8$ aromatic hydrocarbon wherein said catalyst composition is prepared by a process comprising: (1) contacting a zeolite with an aqueous solution of a base at a pH higher than about 10; at a temperature in the range of from about 30 to about 200° C.; and under a pressure in the range of from about 1 to about 10 atm for a period of from about 10 minutes to about 30 hours to produce a base-leached zeolite; (2) separating said base-leached zeolite from the spent aqueous solution; (3) drying said base-leached zeolite; (4) contacting said base-leached zeolite with an aqueous solution containing an acid at a pH lower than about 2; at a temperature in the range of from about 30 to about 200° C.; and under a pressure in the range of from about 1 to about 10 atm for a period of from about 10 minutes to about 30 hours to produce a base-acid-leached zeolite; (5) drying said base-acid-leached zeolite; and (6) recovering said base-acid-leached zeolite; wherein said base is selected from the group consisting of tetramethylammonium hydroxide, tetraethylammonium hydroxide, tetrapropylammonium hydroxide, tetramethylammonium bisulfide, tetraethylammonium bisulfide, lithium hydroxide, sodium hydroxide, sodium hydrosulfide, sodium bisulfide, potassium hydroxide, calcium hydroxide, magnesium hydroxide, sodium bicarbonate, sodium carbonate, sodium oxide, sodium sulfide, magnesium oxide, calcium oxide, calcium carbonate, sodium phenoxide, barium phenoxide, calcium phenoxide, $R^1OM$, $R^1SM$, and combinations of any two or more thereof; where $R^1$ is a $C_1$–$C_{18}$ alkyl radical, and combinations of any two or more thereof and M is an alkali metal, an alkaline earth metal, and combinations of any two or more thereof;

said acid is selected from the group consisting of sulfuric acid, hydrochloric acid, nitric acid, phosphoric acid, ammonium sulfate, ammonium chloride, ammonium nitrate, formic acid, acetic acid, trifluoroacetic acid, citric acid, trichloroacetic acid, p-toluenesulfonic acid, methanesulfonic acid, partially neutralized acids wherein one or more protons thereof have been replaced with a metal, and combinations of any two or more thereof; and said $C_9$+ aromatic compound contains at least 9 carbon atoms.

16. A process according to claim 15 wherein said step (1) of said process is carried out at a pH higher than 12, at a temperature in the range of from about 70 to about 120° C., under a pressure of about 1 atm, and for a period of from 1 to 20 hours; said step (4) of said process is carried out at a pH lower than about 1, at a temperature in the range of from about 70 to about 120° C., under a pressure of about 1 atm, and for a period of from about 1 to about 20 hours; said base is a combination of sodium hydroxide and sodium carbonate; said acid is hydrochloric acid; and further wherein said base-acid-leached zeolite of said step (6) is calcined and contacted with a platinum-containing compound selected from the group consisting of chloroplatinic acid, platinum (IV) chloride, platinum (II) bromide, platinum (II) iodine, tetramine platinum (II) chloride, tetramine platinum (II) nitrate, tetramine platinum (II) hydroxide, tetrachlorodiamne platinum (IV), and combinations of any two or more thereof.

17. A process according to claim 16 wherein said $C_9$+ aromatic compound has the formula of $R_nAr$ wherein each R is a hydrocarbyl radical having 1 to about 15 carbon atoms and is independently selected from the group consisting of alkyl radicals, aryl radicals, alkaryl radicals, aralkyl radicals, alkenyl radicals, and combinations of any two or more thereof, n is a whole number from 1 to 5, and Ar is an aryl group.

18. A process according to claim 17 wherein R is an alkyl radical and said $C_9$+ aromatic compound contains 9 to 12 carbon atoms per molecule.

19. A process according to claim 18 wherein said $C_9$+ aromatic compound comprises an aromatic hydrocarbon selected from the group consisting of 1,2,3-trimethylbenzene, 1,2,4-trimethylbenzene, 1,3,5-trimethylbenzene, 1,2,3,4-tetramethylbenzene, 1,2,3,5-tetramethylbenzene, 1,2,4,5-tetramethylbenzene, n-propylbenzene, 3-ethyltoluene, 4-ethyltoluene, 3-n-propyltoluene, 4-n-propyltoluene, 1,3-diethylbenzene, and combinations of any two or more thereof.

20. A process according to claim 19 wherein said condition comprises a liquid hourly space velocity of said fluid in the range of about 0.1 to about 30 g feed/g catalyst/hour, a gas hourly space velocity of said hydrogen-containing fluid in the range of about 10 ft$^3$ gas/ft$^3$ catalyst/hour to about 5,000 ft$^3$ gas/ft$^3$ catalyst/hour, a molar ratio of hydrogen to said $C_9$+ aromatic compound in the range of about 0.5:1 to about 5:1, a pressure in the range of about 50 psig to about 750 psig, and a temperature in the range of about 250° C. to about 750° C.

21. A process comprising contacting, in the presence of a catalyst composition, a fluid which comprises at least a $C_9$+ aromatic compound with a hydrogen-containing fluid under a condition sufficient to effect the conversion of a $C_9$+ aromatic compound to a $C_6$ to $C_8$ aromatic hydrocarbon wherein said catalyst composition is prepared by a process comprising: (1) contacting a zeolite with an aqueous solution of a base at a pH higher than 12, at a temperature in the range of from 70 to 120° C., under about 1 atm pressure, and for a period of from 1 to 20 hours to produce a base-leached zeolite; (2) separating said base-leached zeolite from the spent aqueous solution; (3) recovering said base-leached zeolite; (4) drying said base-leached zeolite; (5) calcining said base-leached zeolite; (6) contacting said base-leached zeolite with an aqueous solution containing an acid at a pH lower than 0.5, at a temperature in the range of from 70 to 120° C., under about 1 atm pressure, and for a period of from 1 to 20 hours to produce a base-acid-leached zeolite; (7) separating said base-acid-leached zeolite; (8) recovering said base-acid-leached zeolite; (9) drying said base-acid-leached zeolite; and (10) calcining said base-acid-leached zeolite; wherein said base is a combination of sodium hydroxide and sodium carbonate and said acid is hydrochloric acid; and further wherein said base-acid-leached zeolite of said step (10) is contacted with a platinum-containing compound selected from the group consisting of chloroplatinic acid, platinum (IV) chloride, platinum (II) bromide, platinum (II) iodine, tetramine platinum (II) chloride, tetramine platinum (II) nitrate, tetramine platinum (II) hydroxide, tetrachlorodiamne platinum (IV), and combinations of any two or more thereof; and said $C_9$+ aromatic compound contains at least 9 carbon atoms.

22. A process according to claim 21 wherein said $C_9$+ aromatic compound has the formula of $R_nAr$ wherein each R is a hydrocarbyl radical having 1 to about 15 carbon atoms and is independently selected from the group consisting of alkyl radicals, aryl radicals, alkaryl radicals, aralkyl radicals, alkenyl radicals, and combinations of any two or more thereof, n is a whole number from 1 to 5, and Ar is an aryl group.

23. A process according to claim 22 wherein R is an alkyl radical and said $C_9$+ aromatic compound contains 9 to 12 carbon atoms per molecule.

24. A process according to claim 23 wherein said $C_9$+ aromatic compound comprises an aromatic hydrocarbon selected from the group consisting of 1,2,3-trimethylbenzene, 1,2,4-trimethylbenzene, 1,3,5-trimethylbenzene, 1,2,3,4-tetramethylbenzene, 1,2,3,5-tetramethylbenzene, 1,2,4,5-tetramethylbenzene, n-propylbenzene, 3-ethyltoluene, 4-ethyltoluene, 3-n-propyltoluene, 4-n-propyltoluene, 1,3-diethylbenzene, and combinations of any two or more thereof.

25. A process according to claim 24 wherein said condition comprises a liquid hourly space velocity of said fluid in the range of about 0.1 to about 30 g feed/g catalyst/hour, a gas hourly space velocity of said hydrogen-containing fluid in the range of about 10 ft$^3$ gas/ft$^3$ catalyst/hour to about 5,000 ft$^3$ gas/ft$^3$ catalyst/hour, a molar ratio of hydrogen to said $C_9$+ aromatic compound in the range of about 0.5:1 to about 5:1, a pressure in the range of about 50 psig to about 750 psig, and a temperature in the range of about 250° C. to about 750° C.

* * * * *